(12) United States Patent
Mujwid

(10) Patent No.: US 10,076,396 B2
(45) Date of Patent: *Sep. 18, 2018

(54) IMPLANTS, TOOLS, AND METHODS FOR TREATMENTS OF PELVIC CONDITIONS

(76) Inventor: James R. Mujwid, Edina, MN (US)

( * ) Notice: Subject to any disclaimer, the term of this patent is extended or adjusted under 35 U.S.C. 154(b) by 291 days.

This patent is subject to a terminal disclaimer.

(21) Appl. No.: 14/232,043

(22) PCT Filed: Jul. 11, 2012

(86) PCT No.: PCT/US2012/046206
§ 371 (c)(1),
(2), (4) Date: Jan. 10, 2014

(87) PCT Pub. No.: WO2013/009834
PCT Pub. Date: Jan. 17, 2013

(65) Prior Publication Data
US 2014/0171732 A1 Jun. 19, 2014

Related U.S. Application Data

(60) Provisional application No. 61/506,478, filed on Jul. 11, 2011.

(51) Int. Cl.
*A61F 2/00* (2006.01)
*A61B 17/04* (2006.01)
(Continued)

(52) U.S. Cl.
CPC ........ *A61F 2/0063* (2013.01); *A61B 17/0401* (2013.01); *A61F 2/0045* (2013.01);
(Continued)

(58) Field of Classification Search
CPC ......... A61F 2/0004–2/0077; A61F 2210/0057; A61F 2250/007; A61F 2250/0012;
(Continued)

(56) References Cited

U.S. PATENT DOCUMENTS 5,112,344 A 5/1992 Petros
5,611,515 A 3/1997 Benderev et al.
(Continued)

FOREIGN PATENT DOCUMENTS

EP 2691047 A1 2/2014
WO WO2001/62183 8/2001
(Continued)

OTHER PUBLICATIONS

Office Action for European Application No. 12812093.8, dated Jan. 25, 2017, 4 pages.

*Primary Examiner* — Catherine B Kuhlman
(74) *Attorney, Agent, or Firm* — Brake Hughes Bellermann LLP

(57) ABSTRACT

Described are devices, systems, and combinations useful for monitoring tension in an implant, which may be an implant useful to treat pelvic condition, the device, system, or combination including an implant and a tension indicator. Embodiment of tension indicators ca include one or more of a cursor, a reference, or both, to indicate a tension, the cursor or reference taking any useful form or structure, such as multiple color markings printed or otherwise included at a location of the tension indicator or implant. Colored markings can allow for quick and easy indication of a desired implant tension during deployment and positioning. The tension of the implant can be correlated to elongation of a segment of the implant (e.g., implant material) at which the tension indicator is located.

20 Claims, 6 Drawing Sheets

(51) Int. Cl.
*A61B 17/00* (2006.01)
*A61B 90/00* (2016.01)

(52) U.S. Cl.
CPC ............... *A61B 2017/00805* (2013.01); *A61B 2017/00862* (2013.01); *A61B 2017/0414* (2013.01); *A61B 2017/0417* (2013.01); *A61B 2017/0464* (2013.01); *A61B 2017/0496* (2013.01); *A61B 2090/064* (2016.02); *A61F 2250/0073* (2013.01); *F04C 2270/041* (2013.01)

(58) Field of Classification Search
CPC . A61F 2250/0096–2250/98; A61F 2002/4666; A61F 2002/7635; A61B 2090/064–2090/66
USPC .................................................. 600/29–31, 37
See application file for complete search history.

(56) References Cited

U.S. PATENT DOCUMENTS

| | | | |
|---|---|---|---|
| 5,842,478 A | 12/1998 | Benderev et al. | |
| 5,860,425 A | 1/1999 | Benderev et al. | |
| 5,899,909 A | 5/1999 | Claren et al. | |
| 6,039,686 A | 3/2000 | Kovac | |
| 6,042,534 A | 3/2000 | Geilman et al. | |
| 6,110,101 A | 8/2000 | Tihon et al. | |
| 6,612,977 B2 | 9/2003 | Staskin et al. | |
| 6,648,921 B2 | 11/2003 | Anderson et al. | |
| 6,685,620 B2* | 2/2004 | Gifford, III | A61B 17/00234 600/16 |
| 6,691,711 B2 | 2/2004 | Raz et al. | |
| 7,025,063 B2 | 4/2006 | Snitkin et al. | |
| 7,070,556 B2 | 7/2006 | Anderson et al. | |
| 7,280,730 B2 | 10/2007 | Dong et al. | |
| 7,303,525 B2 | 12/2007 | Watschke et al. | |
| 7,347,812 B2 | 3/2008 | Mellier | |
| 7,351,197 B2 | 4/2008 | Montpetit et al. | |
| 7,407,480 B2 | 8/2008 | Staskin et al. | |
| 7,422,557 B2 | 9/2008 | Arnal et al. | |
| 7,500,945 B2 | 3/2009 | Cox et al. | |
| 7,740,576 B2 | 6/2010 | Hodroff et al. | |
| 2002/0099258 A1* | 7/2002 | Staskin | A61B 17/3468 600/29 |
| 2002/0099259 A1 | 7/2002 | Anderson et al. | |
| 2002/0147382 A1 | 10/2002 | Neisz et al. | |
| 2002/0151762 A1 | 10/2002 | Rocheleau et al. | |
| 2006/0089524 A1* | 4/2006 | Chu | A61B 17/06066 600/37 |
| 2006/0287571 A1 | 12/2006 | Gozzi et al. | |
| 2009/0259092 A1* | 10/2009 | Ogdahl | A61F 2/0045 600/30 |
| 2010/0256442 A1 | 10/2010 | Ogdahl et al. | |
| 2010/0261955 A1 | 10/2010 | O'Hern et al. | |
| 2010/0298630 A1 | 11/2010 | Wignall | |
| 2011/0015477 A1 | 1/2011 | Montpetit et al. | |
| 2011/0034759 A1 | 2/2011 | Ogdahl et al. | |
| 2011/0082328 A1 | 4/2011 | Gozzi et al. | |
| 2011/0112357 A1 | 5/2011 | Chapman et al. | |
| 2015/0305847 A1* | 10/2015 | Roll | A61F 2/0045 600/30 |

FOREIGN PATENT DOCUMENTS

| | | |
|---|---|---|
| WO | WO2002/19945 | 3/2002 |
| WO | WO2005/094741 | 10/2005 |
| WO | WO2006/046950 | 5/2006 |
| WO | WO 2007/016083 | 2/2007 |
| WO | WO2007/097994 | 8/2007 |
| WO | WO2007/149348 | 12/2007 |
| WO | WO2008/057261 | 5/2008 |
| WO | WO2010/093421 | 8/2010 |
| WO | WO2010/101888 | 9/2010 |
| WO | WO2011/072148 | 6/2011 |
| WO | WO2011/082287 | 7/2011 |
| WO | WO2012/134689 | 10/2012 |

* cited by examiner

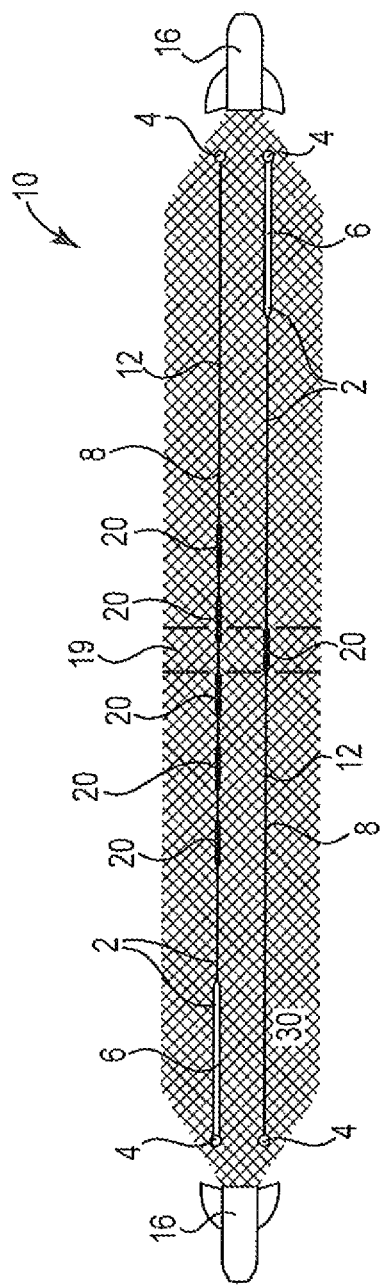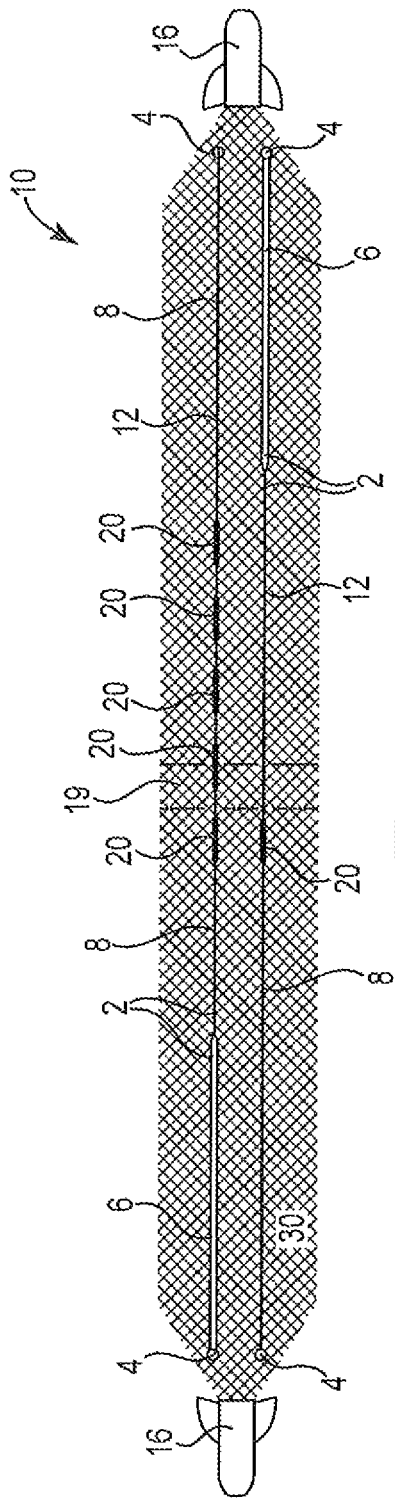

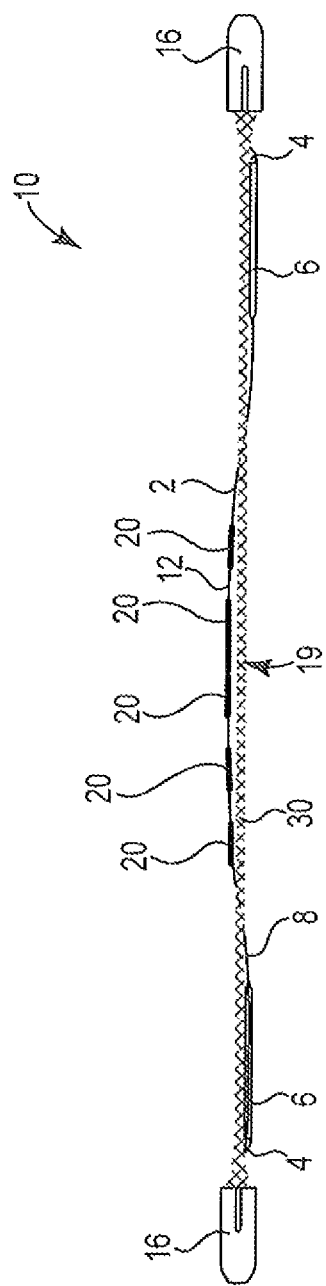

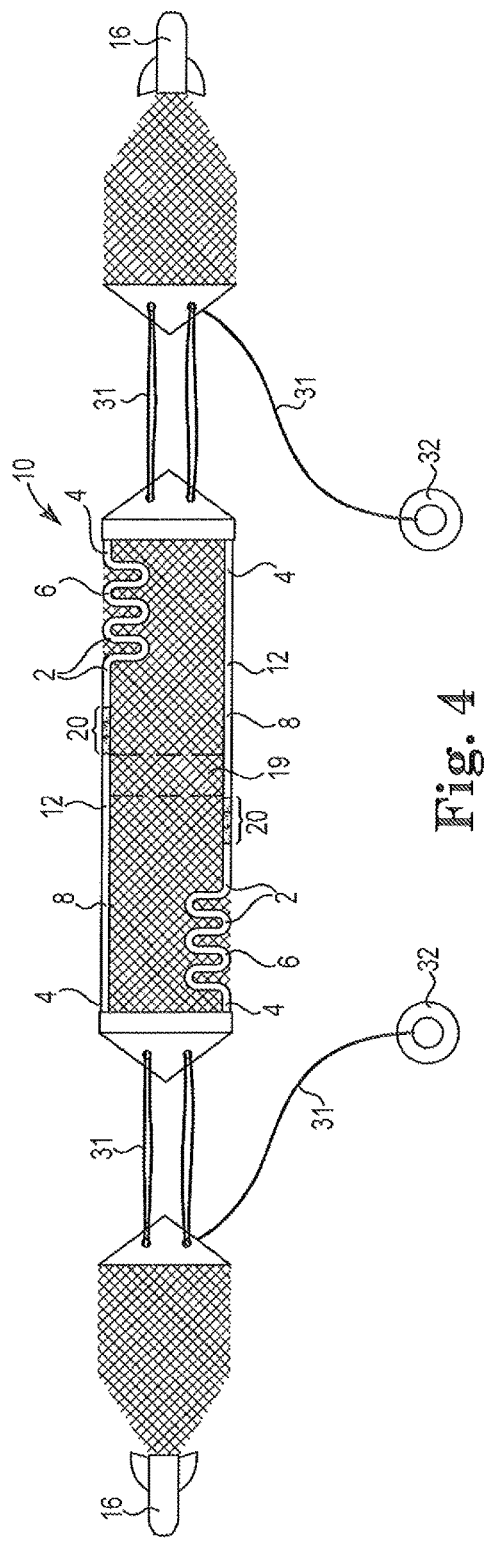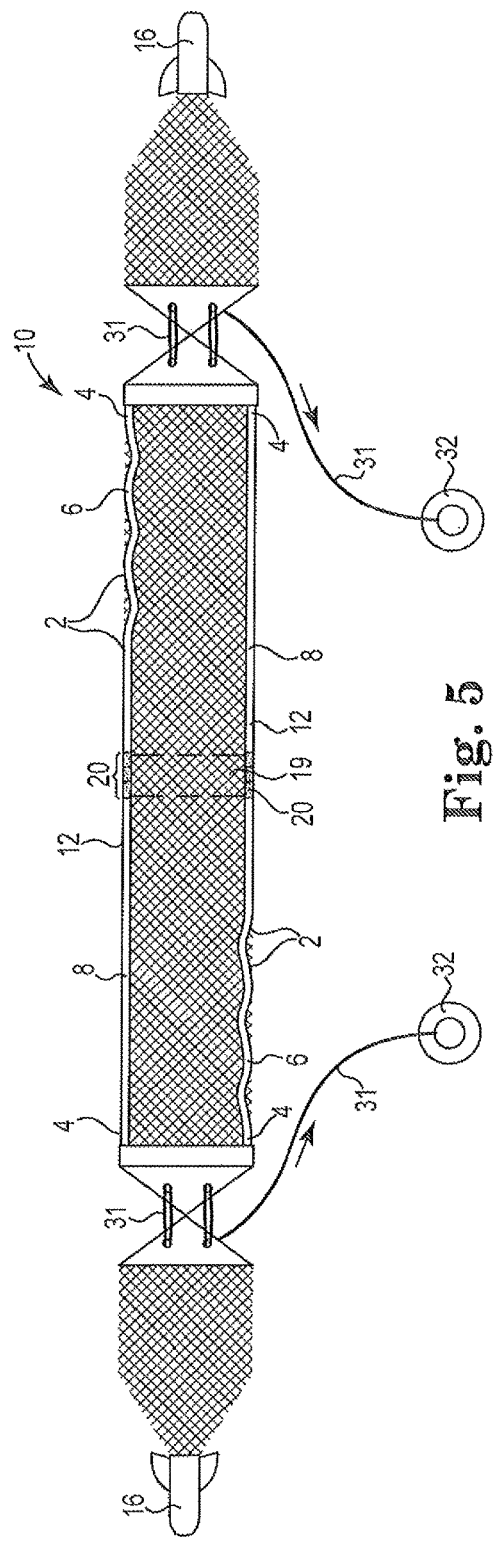

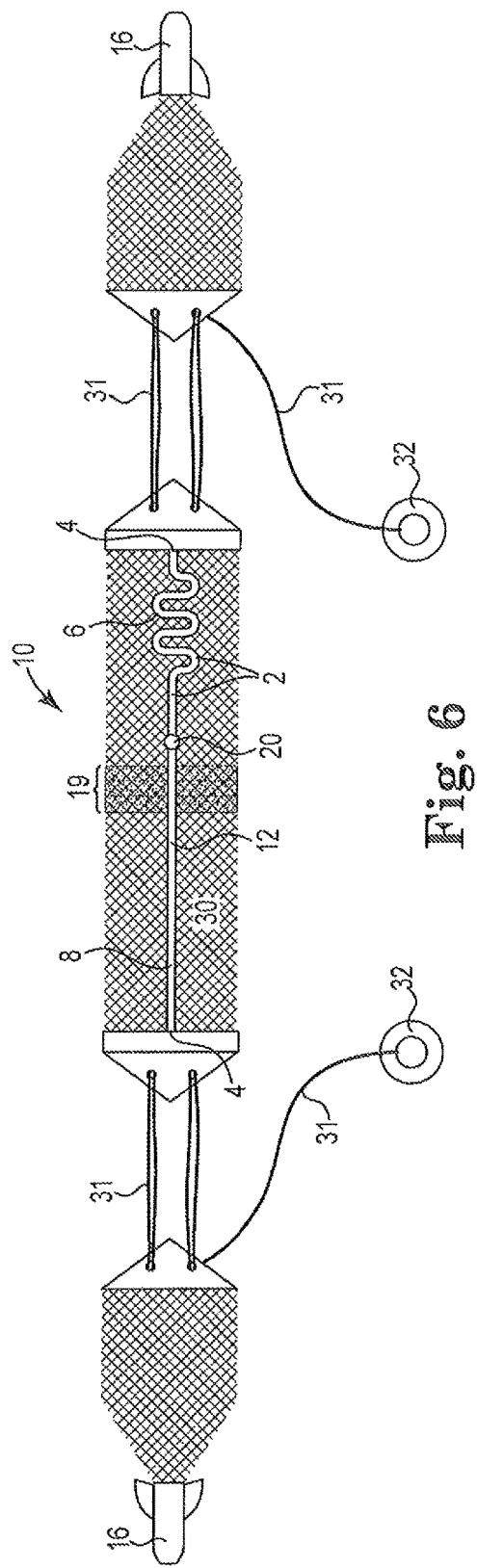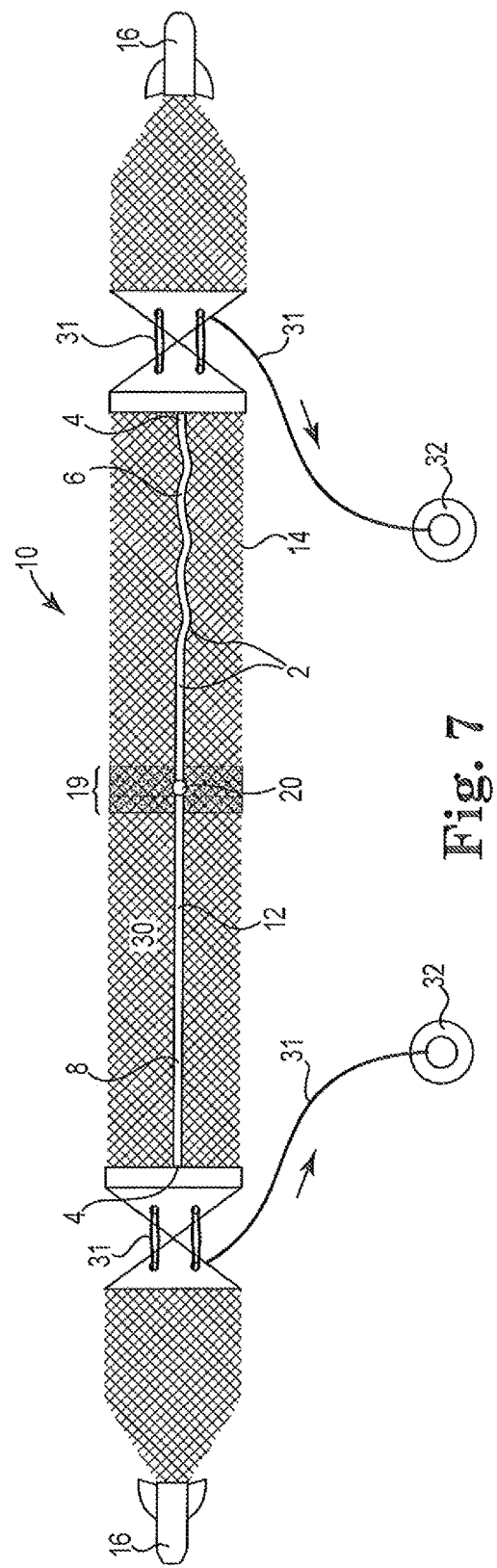

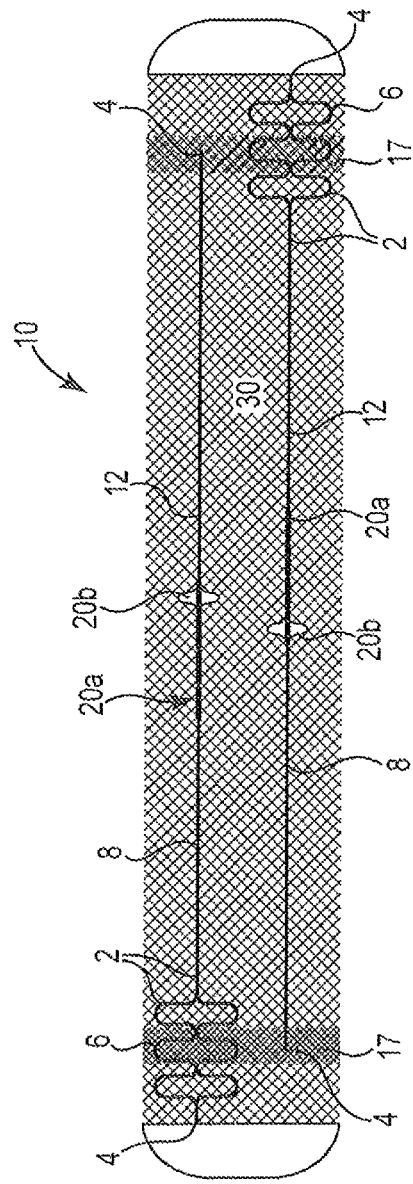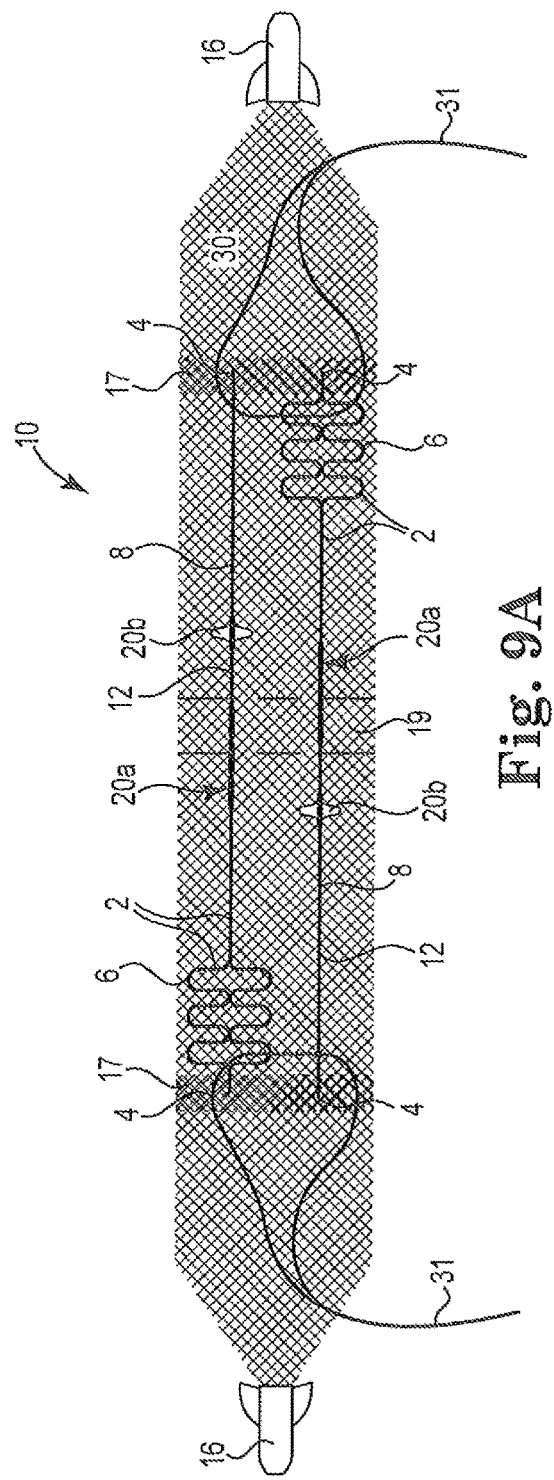

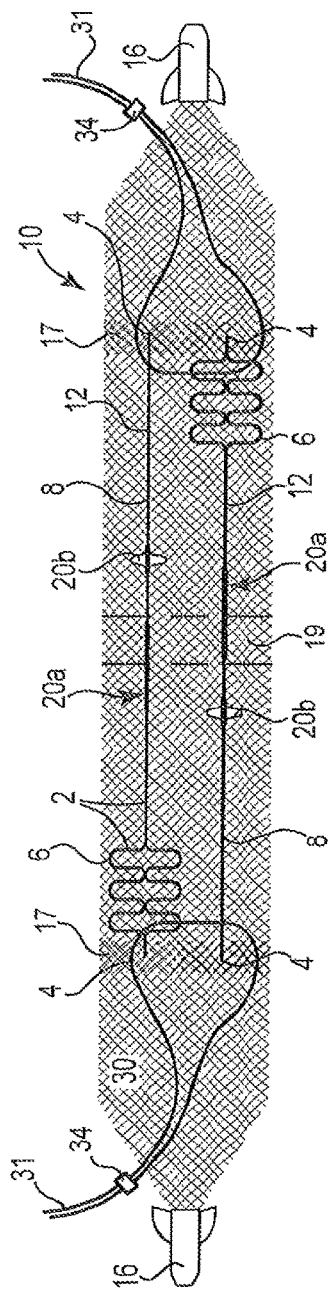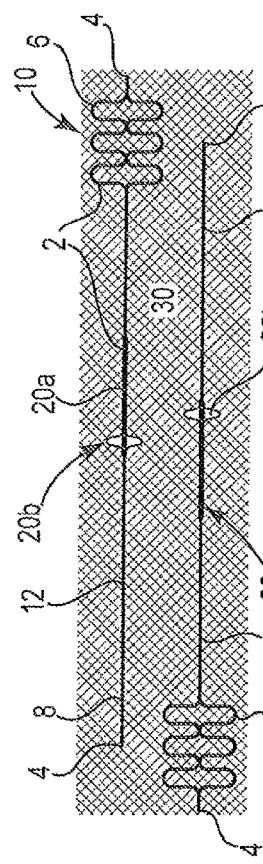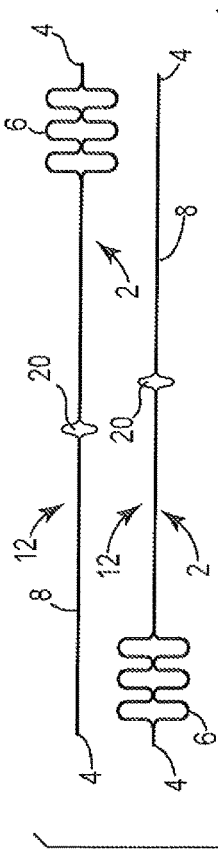

IMPLANTS, TOOLS, AND METHODS FOR TREATMENTS OF PELVIC CONDITIONS

PRIORITY

The present non-provisional patent application claims the benefit from International No. PCT/US2012/046206, which was granted an International filing date of Jul. 11, 2012, which in turns claims priority under 35 U.S.C. § 119(e) from United States Provisional Patent Application having U.S. Ser. No. 61/506,478, filed Jul. 11, 2011, entitled "IMPLANT SYSTEMS WITH TENSIONING FEEDBACK FEATURES," which applications are hereby incorporated by reference in their entireties.

FIELD OF THE INVENTION

The present invention relates generally to implants, tools, devices, systems, apparatus, and related methods for treating pelvic conditions including but not limited to incontinence and prolapse conditions in men and women.

BACKGROUND

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

There is a desire to obtain a minimally invasive yet highly effective supportive implant that can be used to treat conditions that include incontinence, pelvic organ prolapse, and others. Moreover, there is ongoing desire to identify methods and implantable supportive implants that are able to be placed efficiently and effectively within a patient in a manner that provides effective or optimal support, and that can be placed with certain efficacy.

SUMMARY

Devices, systems, and methods as described can be applied to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), levator defects, rectal or fecal incontinence, and other conditions caused by muscle and ligament weakness, hysterectomies and the like.

Embodiments of the implants can include tensioning feedback components, such as visual indicia of tension applied during placement and deployment of the implant.

Embodiment of tension indicators can include one or more of a cursor, a reference, or both, to indicate a tension, the cursor or reference taking any useful form or structure, such as multiple color markings printed or otherwise included at a location of the tension indicator or implant. Colored markings can allow for quick and easy indication of a desired implant tension during deployment and positioning. The tension of the implant can be correlated to elongation of a segment of the implant (e.g., implant material) at which the tension indicator is located.

A tension indicator may include, for example: two ends at fixed locations relative to an implant material, an inextensible segment, and an extensible segment. A material used in the tension indicator or a portion or component thereof may be any useful material, such as a fibrous material (e.g., an inextensible suture), polymer, or metal. Polymeric material (e.g., polypropylene) may be conveniently used for both an extensible segment and an inextensible segment. Polymeric materials allow design flexibility and integrated segments, at the same time.

In certain embodiments, a laser cut film material can define the implant material, with the laser cut film material being heat stacked to polypropylene mesh. Pad printed color indications on mesh or polypropylene laser cut film segments are also envisioned. The disclosed feedback features or mechanisms can be localized to a single center piece or other portion of an implant, or provided along all or a length of an implant, implant material, or implant piece or segment, as is necessary or desired for a particular method of treatment, for example based on an intended method of dissection, placement, or tensioning of an implant.

According to various embodiments, an extensible segment of a tension indicator allows the tension indicator to lengthen, then return to an unlengthened (relaxed) state at which a cursor can be at a centerline or other initial location or marking (e.g., relative to a reference). As the implant is lengthened, a cursor (e.g., coloration or marks on an inextensible segment) remain fixed relative to an end of the tension indicator (e.g., at an attachment point to the implant material). However, a reference located on the implant material (e.g., a centerline marking) will move relative to the cursor. As the implant material lengthens, the movement of the cursor relative to the reference shows overall elongation of the implant material, which can then be correlated to a level of tension in the implant material or a length of the implant material or implant. A reference that includes multiple bands, e.g., color striations, can be used with embodiments of the present invention to assist in determining the degree of tension (elongation change).

In certain embodiments, a single tension indicator with an extensible segment and an inextensible segment can be included on an implant material, with a reference in the form of a color marking being printed onto the implant material (e.g., mesh). This will simplify the assembly process, but also reduce sensitivity due to the use of only a single cursor. In alternate embodiments, two tension indicators (e.g., an upper tension indicator and a lower tension indicator) are placed at a length of an implant material. Each tension indicator includes a cursor, and each cursor can function both as a cursor and as a reference (i.e., a moving reference relative to the other cursor); the two cursors move relative to each other with lengthening of the implant material, in opposite directions relative to the implant material; this provides for increased relative movement and sensitivity between each cursor and the opposing cursor acting as a reference.

Features and devices of the described tension indicators, implants, and methods, may provide advantages over other implants, methods, and systems, including: allowing simple and easy assessment of an implant length or tension; no requirement of additional tools or instruments to determine or provide tension feedback; providing tension feedback as the implant is being placed rather than during a pause and additional step in the procedure; allowing consistent tension of implants between patients by a physician; and use with a large variety of implants and implant materials having consistent elongation through a segment or portion of implant material being tensioned.

Various examples of implantable implants are specifically illustrated, but are not limiting of the present description. Illustrated implants and systems show an implant that can include a (central) support portion and extension portions. Optional anchors or other fixation devices can be included at one or more of the extension portions. Various portions of the implant or a tension indicator can be constructed of polymer materials, such as a laser cut (or molded) thin film or sheet materials of polypropylene, polyethylene, fluoropolymers, or like compatible materials. Illustrated implant systems can be used to treat incontinence or various other conditions, including but not limited to prolapse (various forms) and other conditions or defects of male or female anatomy.

A tension indicator may be non-removable and the indicator and optionally be bioresorbable. Alternately, a tension indicator can include a releasable fastener, which is fastener that attaches a tension indicator to an implant for use in a surgical procedure, and allows the tension indicator to be easily removed from the implant after placement within a patient.

In one aspect the invention relates to an implant material that includes a tension indicator. The implant material has a length that can be increased and decreased. The tension indicator includes: a first end fixed relative to a first position of the implant material, a second end fixed relative to a second position of the implant material, a middle segment extending along a length between the first end and the second end, and a cursor located at the middle segment. When the length of implant material between the first end and the second end is increased, the cursor moves in a first direction relative to a reference. When the length of the implant is decreased, the cursor moves relative to the reference in a direction opposite the first direction.

In another aspect the invention relates to an implant material including a tension indicator. The implant material has a length that can be increased and decreased. The tension indicator includes: a first end fixed relative to a first position of the implant material, a second end fixed relative to a second position of the implant material, a middle segment extending along a length between the first end and the second end, the middle segment comprising an extensible segment and an inextensible segment, and a cursor located at the inextensible segment. When the length of implant material between the first end and the second end is increased, the cursor moves relative to one of the first end and the second end.

In yet another aspect the invention relates to an implant material that includes: extensible implant material, a first tension indicator located along a length of the implant material, a second tension indicator located along a length of the implant material, and a reference.

In another aspect the invention relates to a method of assembling a surgical implant having a tension indicator. The method includes: providing an extensible implant material; providing a tension indicator having a first end, a second end, and a middle segment between the first end and the second end; placing the tension indicator on the extensible implant material; fixing the first end relative to a first position of the extensible implant material; and fixing the second end relative to a second position of the extensible implant material.

In another aspect the invention relates to a method of placing a surgical implant in a patient. The method includes: providing a surgical implant comprising implant material as described herein; placing the implant in a patient while positioning the implant to support tissue; viewing the tension indicator; and adjusting tension of the implant.

In yet another aspect the invention relates to a method of treating urinary incontinence. The method includes: providing a surgical implant that includes implant material as described; creating a medial incision in a male or female patient; dissecting from the medial incision to tissue below a urethra; placing the implant at a location to support the urethra; placing a first end of the implant along a tissue path extending from below the urethra toward a first obturator foramen of the patient; placing a second end of the implant along a tissue path extending from below the urethra toward a second obturator foramen of the patient; and viewing the tension indicator.

BRIEF DESCRIPTION OF THE DRAWINGS

FIGS. 1 and 2 are top views of implant material as described.

FIG. 3 is a side view of an implant material as described.

FIGS. 4 and 5 are top views of implant material as described.

FIGS. 6 and 7 are top views of implant material as described.

FIG. 8 is a top view of implant material as described.

FIGS. 9A and 9B are top views of implant material as described.

FIG. 10A is a top view of implant material as described.

FIG. 10B is a top view of tension indicators as described.

All figures are not to scale.

DETAILED DESCRIPTION

Pelvic floor disorders include urinary and fecal incontinence, prolapse, cystocele, rectocele, enterocele, uterine and vaginal vault prolapse, levator defects, and others, in male and female patients. These disorders typically result from weakness or damage to normal pelvic support systems. Common etiologies include childbearing, removal of the uterus, connective tissue defects, prolonged heavy physical labor, and postmenopausal atrophy.

Vaginal vault prolapse is the distension of the vaginal apex, in some cases to an orientation outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons.

Vaginal vault prolapse is often associated with a rectocele, cystocele, or enterocele. It is known to repair vaginal vault prolapse by suturing to the supraspinous ligament or to attach the vaginal vault through mesh or fascia to the sacrum. Many patients suffering from vaginal vault prolapse also require a surgical procedure to correct stress urinary incontinence that is either symptomatic or latent.

Sling procedures for treating urinary incontinence include surgical methods that place a supportive implant such as a sling to stabilize or support the bladder neck or urethra. A variety of different supportive implants and sling procedures are known. Slings and methods can differ based on the type of sling material and anchoring methods used, and placement and technique for placing and supporting the sling, including tissue to be supported. In some cases, a sling is placed under the bladder neck and secured via suspension sutures to a point of attachment (e.g. bone) through an abdominal or vaginal incision. Other techniques place a supportive portion of a sling below a urethra or bladder neck, and support the sling by placement of ends at or through obturator foramen tissue. Examples of sling procedures for placing pelvic implants are presented in U.S. Pat. Nos. 5,112,344; 5,611,515; 5,842,478; 5,860,425; 5,899,909; 6,039,686, 6,042,534 and 6,110,101; U.S. Publications Nos. 2010/0256442; 2010/0298630; 2011/0034759; 2011/0112357; US 2011/0015477; and 2011/0082328; and PCT Application No. PCT/US12/26888, filed Feb. 28, 2012.

As used herein, an anchor can be any structure that can connect an implant to tissue of a pelvic region. The tissue may be bone or soft tissue such as a muscle, fascia, ligament, tendon, or the like (i.e., supportive tissue). The anchor may be any known or future-developed structure useful to connect an implant to such tissue, including but not limited to a clamp, a suture, a soft tissue anchor such as a self-fixating tip, a bone anchor, and the like.

An implant can include a tissue support portion (or "support portion") that can be used to support a urethra (including a bladder neck), bladder, vagina, levator, rectum, sphincter (e.g., anal sphincter), or other pelvic tissue. Supporting a "urethra" refers to supporting tissue that includes the urethra (which can refer to the bladder neck), and that can optionally include tissue adjacent to a urethra such as bulbospongiosus muscle, corpus spongiosum, or both. According to specific methods involving treatment of urinary incontinence, e.g., in a male patient, a support portion may be placed below bulbospongiosus muscle to support both bulbospongiosus muscle and corpus spongiosum (along with the urethra), or alternately bulbospongiosus muscle may be dissected and a support portion may be placed to contact corpus spongiosum tissue (to support the urethra).

An implant can additionally include one or more extension portion (otherwise known as an "end" portion or "arm") attached or attachable to the tissue support portion. Normally, for treating incontinence, an implant can include two opposing extension portions. Extension portions are elongate pieces of implant material (e.g., mesh, molded implant material, suture, or biologic material) that extend from the tissue support portion and either are or can be connected to the tissue support portion, and are useful to attach to anatomical features or "supportive tissue" in the pelvic region (e.g., using an anchor such as a self-fixating tip or another form of tissue fastener) to thereby provide support for the tissue support portion and the supported tissue. Generally for treating incontinence, two extension portions can extend from opposite ends of a tissue support portion as elongate "ends," "arms," or "extensions," and may attach to supportive tissue in the pelvic region by extending through a tissue path to an internal anchoring point (see, e.g., Applicant's copending United States Patent Application Publication number US 2010/256442, filed Aug. 8, 2008, by Ogdahl, entitled SURGICAL ARTICLES AND METHODS FOR TREATING PELVIC CONDITIONS, the entirety of which is incorporated herein by reference), or may extend to an external incision, such as through an obturator foramen and through an external incision at a groin or inner thigh (see, e.g., Applicant's copending United States Patent Publication Number US 2006/0287571, the entirety of which is incorporated herein by reference). Also see U.S. Patent Publication number US 2011/0034759 and WO 2010/093421, PCT/US2010/057879, filed Nov. 23, 2010, and PCT/US2010/059739, filed Dec. 9, 2010, the entireties of which are incorporated hereby by reference.

In exemplary uses, each extension portion can extend from the location of attachment with the tissue support portion, through pelvic tissue, and optionally attach to supportive tissue within the pelvic region. For certain procedures, the supportive tissue can be tissue adjacent to the urethra such as pelvic fascia; tissue between the urethra and an obturator foramen such as pelvic fascia; or tissue of an obturator foramen such as obturator fascia, obturator internus muscle, obturator membrane, obturator externus muscle, etc. For alternate procedures an extension portion can be sized to extend from the tissue support portion, through an obturator foramen, and to an external incision at an inner thigh region. Other locations for different procedures (e.g., prolapse) include a ligament, tendon, or muscle in the pelvic region such as an arcus tendineus, sacrospinous ligament, or levator muscle.

An implant may include portions, pieces, or sections that are synthetic or of biologic material (e.g., porcine, cadaveric, etc.). Extension portions may be or may include, e.g., a synthetic mesh such as a polypropylene mesh, a suture, a biodegradable suture, a laser cut polymeric film, a molded implant material, or the like. The tissue support portion may be synthetic (e.g., a polypropylene mesh or a molded material) or biologic. Examples of implant products that may be similar to those useful according to the present description include those sold commercially by American Medical Systems, Inc., of Minnetonka Minn., under the trade names Apogee®, Perigee®, and Elevate® for use in treating pelvic prolapse (including vaginal vault prolapse, cystocele, enterocele, etc.), and Sparc®, Bioarc®, Monarc®, MiniArc®, InVance™, and AdVance™ for treating urinary incontinence.

An example of a particular type of pelvic implant is the type that includes supportive portions including or consisting of a tissue support portion and two or four extension portions extending from the tissue support portion. The implant may include multiple pieces, may include an adjusting engagement or an adjusting mechanism to adjust a length or size of the implant, or may be made of implant material consisting of a single integrated piece or strip of molded or mesh material. An implant that has exactly two or four extension portions can be of the type useful for treating urinary incontinence or vaginal prolapse. The term "supportive portions" refers to portions of an implant that function to support tissue after the implant has been implanted and specifically includes extension portions and tissue support portions, and does not include optional or appurtenant features of an implant such as a sheath, tensioning suture, tissue fastener, or self-fixating tip or other type of connector for attaching the implant to an insertion tool.

Dimensions of a tissue support portion can be any dimensions useful to support a specific tissue, e.g., urethral, levator, rectal, or vaginal tissue, for treating a pelvic condition such as incontinence, prolapse, or another pelvic condition. A tissue support portion for use in treating incontinence can be of sufficient length to support and optionally partially surround a urethra or urethra-supporting tissue. A width of a tissue support portion may optionally be greater than a width of extension portions and can be sufficiently wide to increase contact area and frictional forces between a tissue support portion and tissue in contact with the tissue support portion. Exemplary lengths of a tissue support portion can be in the range from 0.5 to 2 inches, such as from 0.75 to 1.5 inches. Exemplary widths of a tissue support portion can be in the range from 0.4 or 0.5 to 4 centimeters, such as from 1 to 2.5 or 3 centimeters. (A tissue support portion may be part of a support portion piece that includes the tissue support portion and optionally some amount of opposing extension portions extending from ends of the tissue support portion. The tissue support portion may be integrally attached to an extension portion with no discrete boundary or separation.)

An implant (e.g., sling) for placement against a corpus spongiosum for treating urinary incontinence in a male patient may optionally and preferably include a widened central support to provide increased contact and frictional engagement with the corpus spongiosum. See, for example, Assignee's copending United States Patent Publication Number US 2006/0287571 and U.S. Pat. No. 7,422,557, the entireties of these applications being incorporated herein by reference.

Dimensions of extension portions can allow the extension portion to reach between a tissue support portion placed to support a pelvic tissue such as tissue of a urethra, vagina, anal sphincter, levator, etc. (at an end of the extension portion connected to the tissue support portion) and a location at which the distal end of the extension portion attaches to supportive tissue at or about the pelvic region. Exemplary lengths of an extension portion for use in treating incontinence, for example, measured between a connection or boundary between the extension portion and the tissue support portion, and a distal end of the extension portion, can be, e.g., from 0.5 to 2.75 inches, preferably from 1.0 to 2.25 inches, and the length can optionally be adjustable. These or other lengths will be useful for implants designed to treat other conditions. As described elsewhere herein, a length of an extension portion may be fixed (i.e., the extension portion does not include any form of length-adjustment mechanism). Alternate embodiments of implants may include an adjusting engagement that allows a physician to alter the length of an extension portion before, during, or after implantation.

Implants as described can include an anchor at a distal end or a distal portion of an extension portion, which is the end or portion not attached to a tissue support portion. (The term "distal" as used in this context generally refers to location at an end of an extension portion away from a tissue support portion.) An anchor or tissue fastener at a distal end or portion of an extension portion can be any of various types, including: a self-fixating tip that is inserted into soft tissue and frictionally retained; soft tissue anchors; biologic adhesive; a soft tissue clamp that can generally include opposing, optionally biased, jaws that close to grab tissue; and opposing male and female connector elements that engage to secure an end of an extension portion to tissue. (See International Patent Application No. PCT/US2007/014120, entitled "Surgical Implants, Tools, and Methods for Treating Pelvic Conditions, filed Jun. 15, 2007; U.S. patent application Ser. No. 12/223,846, filed Aug. 8, 2008, entitled SURGICAL ARTICLES AND METHODS FOR TREATING PELVIC CONDITIONS; U.S. patent application Ser. No. 12/669,099, filed Jan. 14, 2010, entitled PELVIC FLOOR TREATMENTS AND RELATED TOOLS AND IMPLANTS; and WO 2009/075800, the entireties of which are incorporated herein by reference.) An implant may also have one or more extension portion that does not include a tissue fastener or anchor, for example if the distal end is designed to be secured to tissue by other methods (e.g., suturing), or is intended to pass through an external incision, in which case the extension portion may optionally include a connector, dilator, or dilating connector, which connects to an elongate tool that can be used to either push or pull the connector, dilator, or dilating connector through a tissue path (e.g., to an external incision).

One embodiment of a tissue fastener or anchor is a self-fixating tip. A "self-fixating tip" in general can be a structure (sometimes referred to as a soft tissue anchor) connected at a distal end of an extension portion (or extension portion piece) that can be implanted into soft tissue (e.g., muscle, fascia, ligament, etc.) in a manner that will maintain the position of the self-fixating tip and support the attached implant. Exemplary self-fixating tips can also be designed to engage an end of an insertion tool (e.g., elongate needle, elongate tube, etc.) so the insertion tool can be used to push the self-fixating tip through and into tissue for implantation, preferably also through an incision to reach the interior of the pelvic region, e.g., at a location of an obturator foramen or other supportive tissue. The insertion tool may engage the self-fixating tip at an internal channel of the self-fixating tip, at an external location such as at an external surface of the base, at a lateral extension, or otherwise as desired, optionally in a manner to allow the insertion tool to push the self-fixating tip through an incision in a patient and through and into supportive tissue.

Exemplary self-fixating tips can include one or more lateral extensions that allow the self-fixating tip to be inserted into soft tissue and to become effectively anchored in the tissue. A lateral extension may be moveable or fixed. The size of the self-fixating tip and optional lateral extensions can be useful to penetrate and become anchored into the tissue. Exemplary self-fixating tips are described in Assignee's copending international patent application PCTUS2007/004015, filed Feb. 16, 2007, titled Surgical Articles and Methods for Treating Pelvic Conditions, the entirety of which is incorporated herein by reference. Other structures may also be useful.

According to exemplary embodiments, a self-fixating tip can have structure that includes a base having a proximal base end and a distal base end. The proximal base end can be connected (directly or indirectly, such as by a connective suture) to a distal end of an extension portion. The base extends from the proximal base end to the distal base end and can optionally include an internal channel extending from the proximal base end at least partially along a length of the base toward the distal base end. The optional internal channel can be designed to interact with (i.e., engage, optionally by means of a release mechanism that can be selectively engaged and released) a distal end of an insertion tool to allow the insertion tool to be used to place the self-fixating tip at a location within pelvic tissue of the patient. A self-fixating tip can be made out of any useful material, generally including materials that can be molded or formed to a desired structure and connected to or attached to a distal end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA.

According to various systems as described, one or more instrument, insertion tool, adjusting tool, or the like, may be incorporated or used with an implant or method as described. Examples of useful tools include those that generally include one or more (stationary or moveable) thin elongate, relatively rigid shaft or needle that extends from a handle. The shaft can be a single elongate shaft or multiple separate elongate shafts extending from the handle, or one or more primary shaft that extends from the handle and that contains multiple branch or "tine" shafts that separate at the end of the primary shaft. The handle is located at a proximal end of the device and attaches to one end (a proximal end) of a shaft. According to some embodiments, a distal end of one or more shaft can be adapted to engage a portion of an implant such as a tissue fastener (e.g., a self-fixating tip), in a manner that allows the insertion tool to engage and push the tissue fastener through a tissue passage and connect the tissue fastener to supportive tissue of the pelvic region. Examples of this type of tool can be used with a self-fixating tip that includes an internal channel designed to be engaged by a distal end of an insertion tool to allow the self-fixating tip to be pushed into tissue. Other general types of insertion tools will also be useful, but may engage a self-fixating tip or other tissue fastener in an alternate manner, e.g., that does not involve an internal channel.

Exemplary insertion tools for treatment of incontinence and vaginal prolapse are described, e.g., in U.S. patent application Ser. Nos. 10/834,943, 10/306,179; 11/347,553; 11/398,368; 10/840,646; PCT application number 2006/028828; PCT application number 2006/0260618; WO 2010/093421, and US Patent Publication No. 2010-0256442 the entireties of these documents being incorporated herein by reference.

A tool according to the invention can optionally include a mechanism (a "release mechanism") by which a tissue fastener (e.g., a self-fixating tip) can be securely and releasable engaged with a distal end of an insertion tool such that the tissue fastener can be selectively secured to the distal end mechanically, then selectively released. With a releasable engagement, a tissue fastener (e.g., self-fixating tip) can be released from the distal end by releasing the engagement (e.g., mechanical engagement) by movement of an actuator at the proximal end of the insertion tool, such as at the handle. For example, an internal channel (or external surface) of a self-fixating tip can include an engaging surface designed to engage a mechanism at a distal end of an insertion tool while the self-fixating tip is placed at, on, or over the distal end. As an example, an internal or external surface of a self-fixating tip can include a depression, ring, edge, or ledge, that can be rounded, angular, etc. A mechanical detent such as a pin, ball, spring, deflector, or other surface or extension located at the distal end of the insertion tool can be moved, deflected, retracted, or extended relative to the distal end of the insertion tool to contact the surface of the self-fixating tip to securely and releasably hold the self-fixating tip at the distal end of the insertion tool and prevent removal of the tip from the distal end until removal is desired. The detent (or other surface or mechanism) can be cause to extend (or retract) from the distal end of the insertion tool by actuating a trigger or other mechanism located at the proximal end (e.g., handle or a proximal location of a shaft) of the insertion tool, to secure (or release) the self-fixating tip. Upon placement of the self-fixating tip at a desired location during a surgical implantation procedure, the insertion tool operator can release the self-fixating tip by use of the trigger or other mechanism at the handle to disengage the detent and cause the tip to become loose. The insertion tool can then be removed from the tissue path and the self-fixating tip can remain in a desired implanted location.

An implant may have an adjustable length. For example, an implant may include a single piece of mesh and may include a suture or other cinching mechanism that may be actuated (e.g., pulled) to cause a length of a portion of the implant to shorten. The suture can be woven through a length of an implant or piece of an implant in a manner that allows the suture to be tightened to reduce a length of the implant. In other examples, an implant can include multiple pieces that are connected by an adjustable connector such as a suture. The suture can connect two pieces of the implant in a manner that allows the suture to be tightened to reduce a distance between the two pieces of the implant.

Alternate implant embodiments may include multiple pieces connected together at an adjusting engagement. According to some embodiments, an implant can include multiple pieces that are adjustably connected together at an adjusting engagement. A "multi-piece" implant refers to an implant that includes a "support portion piece" and one or multiple "extension portion pieces" as separate pieces of the implant. An extension portion piece can be separate from a support portion piece, and the two pieces can be connected through an adjustable engagement. The support portion piece includes a tissue support portion.

An adjusting engagement may be for example a one-way adjusting engagement, a two-way adjusting engagement, or a locking two-way engagement, that allows a portion, piece, or a segment of an implant to be moved relative to another portion, piece, or segment of the implant, and to be adjusted as to length, tension, or positioning. Examples of adjusting engagements are described, for example, in Applicant's copending U.S. patent application Ser. No. 12/308,436, filed Dec. 15, 2008, entitled SURGICAL IMPLANTS AND TOOLS FOR TREATING PELVIC CONDITIONS, and U.S. patent application Ser. No. 12/669,099, filed Jan. 14, 2010, entitled PELVIC FLOOR TREATMENTS AND RELATED TOOLS AND IMPLANTS, the entireties of which are incorporated herein by reference.

Some adjusting engagements can allow two-way movement of one piece relative to another piece (e.g., a "two-way" adjusting engagement). This type of adjusting engagement allows easy movement of two pieces of an implant, in two directions. The two-way engagement allows a segment of implant (e.g., a segment or portion of an extension portion piece) to move freely in two directions through an adjusting engagement included on a different piece or segment of the implant. The force needed to move the segment of implant in one direction is substantially equal to the force needed to move the segment in the opposite direction, and, optionally, the two-way adjusting engagement does not substantially hinder the movement of a segment of implant through the adjusting engagement with frictional surfaces such as extensions (e.g., "teeth") extending into an aperture through which the segment of implant is moved. As an example, a two-way adjusting engagement may include an open (smooth) aperture that may be circular, oval, square, elongate, or rectangular, such as in the form of a circle, slit, or slot, etc. The aperture may optionally be reinforced by a reinforced perimeter of a shape that is similar to the aperture, such as by a fabric or a polymeric material such as a grommet (e.g., a "loose grommet" or "eyelet"), which may be circular, square, rectangular, or of any desired shape. The reinforced perimeter (e.g., grommet) defines a reinforced aperture through which a segment of implant can pass relatively freely and with the same resistance two different directions. A two-way adjusting engagement may optionally be capable of an open and a closed (e.g., locked) configuration, the open configuration allowing two-way movement between the pieces, and the closed (or locked) configuration preventing any movement between the pieces.

Other adjusting engagements may allow for one-way adjustment such as shortening of a length of an extension portion. These adjusting engagements can be referred to as "one-way" adjusting engagements, and allow adjustment of a length of an implant portion (e.g., extension portion) in one direction and not (or not easily) in an opposite direction. An exemplary one-way adjusting engagement can include an aperture through which a segment of implant (e.g., a portion of an extension portion piece) can extend, and one or multiple surfaces (e.g., extensions or teeth) that frictionally engage the segment of implant passing therethrough, e.g., by extending into or toward the aperture or otherwise contacting the segment of implant to inhibit movement of the segment of implant relative to the adjusting engagement. The one-way engagement can preferentially allow movement of the segment of implant through the aperture in one direction while inhibiting or preventing movement of the segment of implant in an opposing direction.

One form of implant useful for treatment of urinary incontinence is a "mini-sling" or "single incision sling," (e.g., as marketed by American Medical Systems under the trade name MINIARC™). Designs described herein are also useful for female pelvic floor repair products, male incontinence, for treating prolapse (e.g., vaginal prolapse), levator defects, anal incontinence, and other pelvic conditions.

A feature of an implant as generally described herein is a tension feedback indicator (or, herein, "tension indicator" or "indicator"). A tension feedback indicator is a device associated with an implant that allows for a user (e.g., surgeon or doctor) to identify a level of tension applied to an implant or portion of an implant such as an extension portion or a tissue support portion, during a surgical procedure in which the implant is placed in a patient. Certain tension feedback indicators as described herein can allow for simple visual indication of tension applied to an implant, implant material, implant segment (e.g., a mesh, biologic, or a molded material), or the like during a surgical procedure. Any of the tension feedback indicators described can be used with any implant that, during installation, includes a tension or length that is desirably measured, gauged, or quantitatively or qualitatively assessed; these include any of the implants generically or specifically described herein that either include or do not include an adjustment mechanism (e.g., an adjusting engagement or other form of adjustment mechanism), any implant previously or presently known to be useful for treating a pelvic condition, and implants developed in the future for treating a pelvic condition.

A tension indicator can allow for simple and easy measurement and indication of an amount of tension placed on a length of implant or a piece or portion of an implant or implant material (e.g., an extension portion or a tissue support portion) during surgical placement of the implant in a patient. No additional tool or instrument is needed, as feedback is provided by the tension indicator located on the implant itself. The feedback is provided as the implant is being placed, so there is no need to pause during placement to check tension then re-engage and finish placement. A surgeon is able to apply consistent tension during placement of an implant. The tension indicator can be attached to any type of implant provided that the implant material has consistent or predictable elongation through the measured segment of implant material being tensioned.

The tension indicator can be a device placed onto a portion of an implant, such as a length of an elongate portion of an implant, that will be affected based on the degree of tensioning of the implant. Generally a length of implant will stretch or lengthen when tension is placed on the length of implant. A tension feedback indicator, fixed relative to two locations along the length of implant, can change form based on the changing or changed length of the implant. As an example, a tension indicator may change in shape or dimension, such as by lengthening, or by deforming or extending an extensible segment (e.g., spring), upon tensioning of an implant material to which the tension indicator is attached. The degree or extent of the change in dimension or shape can be correlated to an amount of tension that is being placed along the length of implant.

A tension indicator can include an overall structure that includes a middle segment located along a length of the tension indicator between two ends. The two ends are fixed relative to two locations of the implant, such as by being directly or indirectly attach to the implant. The middle segment can be extensible, e.g., can include one or more extensible (e.g., deformable) segment (e.g., a spring) that allows a length of the tension indictor to increase when the tension indicator is pulled length-wise, for example when tension is applied by pulling the ends of the tension indicator in opposite directions. The middle segment can also include a non-extensible (inextensible) segment. The middle segment returns substantially to an original size, shape, and form when allowed to, such as when tension is removed. When the ends are attached to an implant and the implant is lengthened, the extensible segment of the middle segment is elongated (e.g., deformed) in a manner that allows the middle segment to become lengthened, and the ends remain fixed relative to their original positions on the implant, as the implant lengthens. The extensible segment allows the indicator to lengthen upon lengthening of the implant to which the tension indicator is attached, and can preferably return to a non-lengthened form when tension in the implant is released.

An extensible segment can include any structure or material that can be extended in a longitudinal (lengthwise) direction, e.g., along a longitudinal axis of the extensible segment, which will generally align with a longitudinal axis of the tension indicator, and be parallel to a longitudinal (length-wise) axis of the implant. The extensible segment may be extended by applying a lengthening force to the extensible segment, for example by applying a net force in opposite directions at two ends of the extensible segment. The force is preferably insufficient to permanently deform the structure of the extensible segment, and when the force is removed, the extensible segment will return substantially to its original form and length.

Examples of extensible segments include linear elastomeric structures such as linear pieces of rubber or other natural or synthetic polymer (e.g., silicone), a rubber band or similar elastomeric material, elastic fabric, an elastic or elastomeric tube, and the like, e.g., in the form of an elongate line, strip, ribbon, band, fiber, etc. When opposing (tensioning) forces are applied to two ends of the linear elastomeric structure, the structure will elongate to increase in length; when the force is removed the linear elastomeric structure will return substantially to an original size and form.

Other examples of extensible segments include non-linear shape-deformable structures (or simply "deformable structures," meaning, for the present purposes, non-permanently deformable structures) that include a non-linear structure such as a deformable two or three-dimensional spring that can be increased in length by application of a net lengthwise force to two ends of the shape-deformable structure. The lengthwise force produces strain in the deformable structure, non-permanently changing a shape of the shape-deformable structure and extending a length of the structure between two ends. When the force is removed the shape-deformable structure will return substantially to original form and length.

A shape-deformable structure may be formed of metal or polymeric (e.g., plastic) materials, and may be made by techniques such as casting, molding, extruding, setting (e.g., by curing, thermoforming, etc.), bending, cutting (e.g., die cutting or laser cutting), etc. A shape-deformable structure can include a length and a longitudinal axis along the length. The structure can be lengthened in a direction of the longitudinal axis by application of a length-wise tensioning force to produce non-permanent deformation in a lengthwise direction. The shape-deformable structure can include one of any useful non-linear forms that can be deformed to increase a length of the structure, such as corners, straight sections, curves, angles, or undulations, in three or (preferably) two dimensions, such that the shape-deformable structure is biased to maintain an unstrained, un-stretched, unlengthened, or "relaxed" length, but is capable of being lengthened by non-permanent deformation by opposing forces placed longitudinally at the ends in opposite directions; when the forces are released the segment returns substantially to the original un-stretched (relaxed) length.

A shape-deformable structure can be any structure that functions as described, and may be molded, die cut, cast, extruded, cut (e.g., laser cut), or bent, and made of any useful material such as a polymer, polymeric film, metal, fiber, or combination of two or more of these. Useful materials include flexible (non-rigid) polymeric materials such as polyolefin, polyester, nylon, polyurethane, polypropylene, and other similar non-biodegradable or biodegradable polymeric materials known to be useful for preparing surgical devices or instruments.

A middle segment can also include an inextensible segment. The inextensible segment can be a segment of the middle segment that experiences essentially no extension when placed under tension, e.g., less than one percent extension when the segment is subjected to manual tensioning forces of a type and magnitude encountered during surgical placement of the implant and use of the tension indicator to measure tension. An inextensible segment can be made of any inextensible material, and can be a non-linear or (preferably) linear segment of material having two ends. One end is fixed at a fixed location relative to the implant, e.g., fixed or secured directly or indirectly to the implant, and the other end can connect to an end of the extensible segment. Examples of materials and structures for inextensible segments include elongate, e.g., linear (alternately non-linear), straight pieces of rigid or non-rigid inextensible (under tension) material such as: an inextensible polymeric line (e.g., extruded, woven, wound, knit, cast, cut, molded, etc.); a metal wire, strip, rod, etc.; and a fiber line such as a thread, suture, or other linear, natural or synthetic (e.g., polymeric) material. Useful polymers include polyolefins, polyester, nylon, polyurethane, polypropylene, and other similar non-biodegradable or biodegradable polymeric materials known to be useful for preparing surgical devices, implants, or instruments. The inextensible segment can be formed by any method, such as by standard die cutting or laser cutting of a polymeric film, extrusion, or by molding a polymeric material into the form of an inextensible segment.

During use, an extensible segment and an inextensible segment of a middle segment of a tension indicator can work together to allow the tension indicator to extend upon length-wise extension of an implant or implant material. When an implant material is lengthened, force is applied at two ends of the middle segment, each end being located at a fixed location relative to (e.g., attached to) the implant or implant material. The force pulls the ends of the middle segment in opposite directions. The force causes the extensible segment to increase in length, e.g., by non-permanent shape deformation or by elastic elongation. But the inextensible segment does not substantially increase in length. The change in length of the middle segment is due essentially entirely to extension of the extensible segment, with the inextensible segment experiencing essentially no change in length.

According to certain specific embodiments, a feedback indicator can include a cursor, a reference, or a cursor and a reference, each of which either alone or together can allow for quick and easy assessment of a desired level of tension applied to an implant during a surgical procedure.

A cursor can be a structure on a middle segment of a tension indicator, such as at an inextensible segment, that can be identified visually. Specific examples of structures that may act as a cursor include a single structural feature or a set of features located at a middle segment of a tension indicator, such as a boundary, line, marking (e.g., printed or structural marking such as a colored area or line), arrow, point, angle, needle, bulb, ball, knot (e.g., a knotted length of ribbon, thread, or suture, optionally colored), shape (square, triangle, circle), opening, etc., or a series or combination of these.

A reference can be a physical structure or marking (indicia such as a colored line or band) (one or multiple) present on a tension indicator or at another location of the implant such as directly on an implant material. An amount of tension placed on the implant at a location of the tension indicator can be correlated to a change in length (i.e., the elongation) of the implant segment, which can in turn be indicated by the tension indicator by a comparison of the location of the cursor to one or more physical references (e.g., demarcation, structure, indicia, or the like) located on the implant, on the tension indicator, or on a combination of these.

The reference may include one or a series of demarcations relative to which a cursor will move upon lengthening of the tension indicator. A reference may generally be any marking, such as coloration or one or multiple molded, cut, or attached physical structures of an implant, implant piece or portion (e.g., mesh), or tension indicator. A reference for one tension indicator may optionally be in the form of a cursor of another tension indicator, if an implant includes two tension indicators. Specific examples of structures that may act as a reference include a single structural feature or a set of features of a backer, such as an aperture, a boundary, curved or straight line, marking, arrow, point, angle, needle, bulb, ball, knot (e.g., a knotted length of ribbon, thread, or suture, optionally colored), shape (e.g., square, triangle, circle), opening, etc., or a series or combination of these. An alternate form of a reference can be a printed reference located at a fixed position on an implant or implant material, such as a midline marking or a series of markings that includes the midline marking. A printed reference may be a single marking or a series of marks that allows the relative location of a cursor to be visually compared to the reference.

To provide for improved potential for visualizing a cursor and a reference, a cursor and a reference can be located at a location of an implant that can be visible through a surgical incision. For treating incontinence, a cursor or reference can optionally be located at or about a midpoint or midline of a length of an implant, e.g., at a location that will be at or near a midline of the patient, e.g., at a urethra, when the implant is being placed therapeutically.

A tension feedback indicator can be a device having dimensions on a scale of a portion of an implant, e.g., on a scale of a support portion or an extension portion, and can be sized to be attached to a portion of implant such as along a length of an extension portion or at a support portion. A width of a tension indicator can be as small as a single line or suture or length of extensible polymeric material. A slightly larger width dimension can be associated with an extensible segment that includes a two- or three-dimensional spring segment. In preferred embodiments, a width of a tension indicator can be sufficiently small to allow one or optionally two tension indicators to be placed in parallel, next to each other, on a single side of an elongate implant material. A length of a tension indicator (measured in a relaxed state) can be as desired, and may be shorter than a total length of an implant or portion of an implant at which a tension is being measured. Lengths from 2 to 10 centimeters, e.g., from 2.5 to 8 centimeters or from 3 to 7 centimeters may be useful, with lengths outside of these ranges also possibly useful depending on dimensions of an implant and of a portion of implant of which tension is desirably measured. The length and extensibility of an extensible segment can be sufficient to allow the length of an implant or implant material to increase by from 20 to 100 percent without permanent deformation of the extensible segment.

The tension indicator, or portions or segments thereof, can be made of any material that allows the tension indicator to function as described herein, e.g., by reversibly changing form or shape upon application of tension along a length of the tension indicator and an attached implant, and being able to substantially return to an original shape upon removal of the tension. Useful materials include flexible (non-rigid) polymeric materials such as polyolefin, polyester, nylon, polyurethane, polypropylene, and other similar non-biodegradable or biodegradable polymeric materials known to be useful for preparing surgical devices or instruments; metals; fibrous materials such as thread or suture materials, and others. The tension indicator can be formed by any method, such as by standard die cutting or laser cutting of a polymeric film, by molding a polymeric or metal material into the form of a tension feedback indicator or segment thereof, or by assembling multiple segments or pieces (e.g., an extensible segment and an inextensible segment) by use of molding (e.g., insert molding), extrusion, tying, adhesives, and the like.

A preferred tension indicator for use with a polypropylene implant material (e.g., polypropylene mesh or molded polypropylene) may be made from materials that include polypropylene. By using the same material for the tension indicator as for the implant (e.g., polypropylene), a process of joining the tension indicator to the implant might be simplified. Also, by optionally using the same material for an extensible segment and an inextensible segment, such as a cut, extruded, or molded polymer (e.g., polypropylene film or other like materials), an extensible segment and an inextensible segment can be efficiently designed and prepared as integrated features of a tension indicator. This may advantageously result in design flexibility and an integrated attachment of an extensible segment to an inextensible segment.

Each end of a tension indicator can be fixed relative to a location of the implant or implant material. The ends can be securely fixed and directly attached to the implant material, if desired, by any securing means, including by tying an end of the tension indicator to implant material, by heat bonding, by adhesive, or by connecting through another structure such as a frame. Alternately and optionally, a tension indicator may be removable from the implant material. Removable securing means (e.g., a releasable fastener) can be used to removably secure an end of the tension indicator to an implant material to allow the tension indicator to be released from the implant material and removed from the implant material, and the patient, after use of the tension indicator during a surgical procedure. See Applicant's co-pending PCT patent application PCT/US2012/026888, filed Feb. 28, 2012, the entirety of which is incorporated herein by reference.

A "releasable fastener" is a fastener that can be operated on manually (including by use of a surgical tool such as a scissors) (after the implant has been implanted in a patient) to release the fastener and the tension indicator from the implant and allow the tension indicator to be removed from the patient. The implant remains in the patient and will function to support tissue after the tension indicator is removed.

Examples of releasable fasteners include fasteners that include an attached suture or other tether (which can be removed or pulled out when desired to release the fastener), ultrasonic bonding, thereto-bonding, adhesive bonding, mechanical engagement, a tear-away design using thin film or other bonding methods that allow for a releasable bond, a push-through rivet design that allows ease of assembly and removal, and others. According to certain preferred embodiments, a tension indicator can include two posts (e.g., attachment pegs) at opposite ends of the tension indicator, each post being of a length to extend through the implant from a front side of the implant (at which side the tension indicator is located) to a back side of the implant (at which side an optional suture can attach to the post by way of a removable engagement). A single suture (optionally also a tether) or equivalent structure such as metal, plastic, polymer (natural or synthetic), wire, thread, or filament, can be attached to each of the two posts by passing through one aperture at a distal location of each post. To remove the tension indicator from an implant material (e.g., mesh), the suture can be removed (optionally after cutting) from the posts, and the tension indicator can be removed from the implant material (e.g., mesh) previously surgically placed.

A fastener or attachment mechanism can be made in any form and from any material that allows a tension indicator to be secured as desired (permanently or removably) to an implant. A material can be as desired, including a material as described herein for use in a tension indicator or an implant. In certain embodiments polypropylene may be a useful material for bonding techniques such as ultrasonic welding and heat staking, especially with an implant material made of polypropylene mesh. Alternate attachment mechanisms or fasteners can include mechanical structures such as rivets or pegs (or "extensions" or "standoffs") that can be pushed through an existing aperture (e.g., a pore of a mesh, or an aperture of a molded implant material) of an implant material in a manner to permanently or removably secure a tension indicator to an implant material without additional processing. As specified, an exemplary design that can be used is a post-suture design that uses an attachment peg (post) extending from the indicator. The attachment peg passes through the thickness of the implant material and a suture is used as a pin passing through an aperture at the distal end of the peg, on the side (the back side) of the mesh opposite of the indicator (which is located on the front side) so the suture acts as a cotter pin to secure the tension indicator in place during use. After surgical placement of the implant in a patient, the suture can be removed to allow the tension indicator to be removed.

The attached figures illustrate various embodiments of implants 10 that include one or two tension feedback indicators 12. Each tension indicator 12 includes middle segment 2, ends 4, extensible segment 6 (part of middle segment 2), and inextensible segment 8 (also part of middle segment 2). Each implant 10 includes an implant material (e.g., mesh or molded polymer) 30, and can be considered to include a support portion, two opposing extension portions, and anchors or self-fixating tips 16 at opposing ends. Each tension indicator 12 includes one or more structure that can function as a cursor 20. Each implant includes one or more structure that can function as a reference (colored, structural, or both) 19. Each end 4 is held at a fixed location relative to a location of implant material 30, e.g., by being directly secured to the implant material at a fixed location.

Embodiments of implants 10 can include a center mark (attached material, color, or other visual indicia) 19 as a reference, proximate the center (midline) along a length of the support portion of implant 10. See FIG. 1. Alternately, two or more color indicators 19 in the form of multiple vertical stripes or bands, optionally each of a different color can make up a reference 19. Indicators (references) 19 can be in the form of material attached to implant material 30, such as Tyvek strips, sutures, or other colored ribbon or material. Or, a reference 19 may be a coloration or colored marking placed onto implant material 30. Likewise, cursor 20 can be constructed of a material such as Tyvek strips, sutures, or different colored markings, placed at (e.g., attached to) a location along a length of an inextensible segment of a middle segment; alternate cursors can be polymeric structures molded or cut during formation of inextensible segment 8. Or, a cursor 20 may be a coloration or colored marking in the inextensible segment 8 optionally in the form of multiple different color markings.

Relative movement of cursor 20 against reference 19 can be a visual indication of a level of elongation or tension exerted on implant 10, and can provide a beneficial feedback mechanism for surgical placement and adjustment of implant 10. Upon placement of implant 10 within a patient, implant 10 is put into tension; lengthwise force is placed longitudinally along extensible segment 6 of each tension indicator 12, causing extensible segment 6 to increase in length. Lengthwise force is also placed longitudinally along inextensible segment 8 of each tension indicator 12, but inextensible segment 8, under tension, remains in an original form and dimension without substantially changing length.

In certain illustrated embodiments, reference 19 is located at a midline or center of implant 10. As described, a reference 19 may be located elsewhere, or may be in a different form, such as at any useful location of implant material 30, or at a location of a second tension indicator 12 (see e.g., FIGS. 8, 9A, 9B and 10A). As illustrated, reference 19 in the form of a centerline will generally remain centered relative to a patient. The location of a cursor 20 relative to implant 10, implant material 30, and reference 19, will change as implant 10 elongates, and with lengthening of extensible segment 6 but not inextensible segment 8. Extensible segment 6 returns an original shape, form, and length, when implant 10 returns to an original, un-stretched, un-extended, "free," or "relaxed" state. Optionally, a portion or segment of middle segment 2, e.g., inextensible segment 8 or extensible segment 6, can be passed (e.g., woven) through select pores or openings in implant material 30 to secure positioning of middle segment 2, for example by placing a middle segment 2 at edges or at a centered (width-wise) location on implant 10.

Referring now to FIGS. 1 and 2, implant 10 is shown in a relaxed (unextended) state at FIG. 1 and a lengthened (extended) state at FIG. 2. Implant 10 includes two tension indicators 12, each including ends 4 held at fixed locations relative to implant material 30, extensible segment 6, inextensible segment 8, and one or multiple cursors 20. Extensible segment 6 is illustrated to include a length of elastic, elongatable polymer such as a rubber band, silicone strip, or natural or synthetic elastomeric tube. Inextensible segment 8 is illustrated to include a length of material that does not elongate under tension, such as a fibrous or polymeric thread or suture material. The length and extensibility of extensible segment 6 can be sufficient to allow the length of implant 10 to increase by from 20 to 100 percent without permanent deformation of extensible segment 6. A length of tension indicator 12 (in a relaxed state) can be as desired based on the length of the implant, e.g., from 2 to 10 centimeters. A length of extensible segment 6 (in a relaxed state) may be a portion of the total length, e.g., from 10 to 50 percent, or from 10 to 30 percent, of tension indicator 12. A length of inextensible segment 8 (in a relaxed stated) may be a portion of the total length, e.g., from 50 to 90 percent, or from 70 to 90 percent, of tension indicator 12.

Still referring to FIGS. 1 and 2, implant 10 includes an upper tension indicator 12 and a lower tension indicator 12. Each tension indicator 12 is attached at ends 4 to implant material 30 by any useful attachment technique. For example, an end 4 can be tied to implant material 30, secured by an adhesive, secured by thermobonding, ultrasonic welding, etc.

Multiple cursors 20 of upper tension indicator 12 are a series of markings or attached materials (e.g., colored ribbons or thread, optionally each one being a different color) located at regular intervals along a length of inextensible segment 8, generally at a centered position of implant 10. When implant 10 is lengthened, inextensible segment 8 (of upper tension indicator 12) attached at end 4 (on the right side as illustrated) does not lengthen. Each of cursors 20 of upper tension indicator 12 is pulled in a direction to the right (as illustrated) and moves relative to centerline reference 19.

Lower (as illustrated) tension indicator 12 includes a single cursor 20 in the form of a single marking or attached material (e.g., colored ribbon or thread) located at a central location of implant 10 on inextensible segment 8. When implant 10 is lengthened, inextensible segment 8 (of lower tension indicator 12) attached at end 4 (on the left side as illustrated) does not lengthen. Cursor 20 of lower tension indicator 12 is pulled in a direction to the left (as illustrated) and moves relative to centerline reference 19.

FIGS. 1 and 2 show implant 10 in an unextended state (FIG. 1) and an extended state (FIG. 2) in which opposing ends are pulled in opposite directions along the length of the tension indicator and implant. The extended state occurs when ends (having self-fixating tips 16) are pulled away from each other, such as when self-fixating tips 16 are fastened to supportive tissue during surgical implantation. In use, each self-fixating tip is placed at supportive tissue of a patient and a tissue support portion (approximately at the centerline) supports tissue; for example, in a procedure to treat urinary incontinence in a male or female patient, implant 10 may be passed into a patient through a medial (e.g., vaginal or perineal) incision. A first self-fixating tip 16 can be placed at supportive tissue on a first side of the patient, such as at tissue of an obturator foramen. The tissue support portion is placed to support tissue of a bladder or urethra. The second self-fixating tip can be placed at supportive tissue on a second (contralateral) side of the patient, such as at an opposing obturator foramen. During placement and adjustment of sling 10 to support the urethra, a surgeon may monitor the location of cursors 20 relative to reference 19, as an indication of tension present along the length of implant 10.

FIG. 3 is a side view of implant 10 of FIG. 1 in a relaxed state. This view shows that tension indicator 12 is attached at each of ends 4 to implant material 30, and that at two locations the tension indicators 12 passes through apertures or pores in implant material 30. The center portion of each tension indicator 12 is located on a front of implant material 12, which is the side opposite of the back side (which contacts tissue). Locating tension indicators 12 on the front side prevents their operation from being interfered with due to contact with tissue, and also allows visibility of tension indicators 12, cursor 20, and reference 19, during a surgical procedure.

FIGS. 4 and 5 illustrate tension indicators 10 that include physical features and structures in common with indicator 10 of FIGS. 1, 2, and 3, including two (an upper and a lower) tension indicators 12 extending between ends 4, and including inextensible segment 8 and extensible segment 6. In FIGS. 4 and 5, extensible segment 6 is in the form of a shape-deformable spring comprising a molded or cut polymeric (e.g., polypropylene) segment having undulating curves. The spring can be extended by placement of tension at ends 4 in opposite directions such that undulating curves become non-permanently deformed (see FIG. 5). Inextensible segment 8 is also made of molded or cut polymer, integrally with extensible segment 6, and can be formed in a single molding or cutting step with extensible segment 6.

Implant 10 of FIGS. 4 and 5 includes three pieces: a central piece that includes a tissue support portion and two tension indicators 12, and two end pieces. The central piece includes a length and two opposing ends. At each end of the central piece is attached adjusting suture 31, which is threaded between the end of the central piece and an end piece to produce a length-adjusting mechanism between the end piece and the central piece. The threaded configuration of adjusting suture 31 allows a user to pull tab 32 connected to a proximal end of adjusting suture 31 in a direction away from implant 10 to cause a length of adjusting suture 31 between the central piece and an end piece to shorten. Reference 19 at FIGS. 4 and 5 is a centerline mark, and cursor 20 is a multi-colored marking at a central location of each tension indicator 12, at inextensible segment 8.

FIGS. 4 and 5 show implant 10 with the central piece in an unextended state (FIG. 4), and in an extended state (FIG. 5) in which opposing ends 4 of tension indicators 12 are pulled in opposite directions along the length of the tension indicators 12 and implant material 30. The extended state occurs when ends of central piece are pulled away from each other, toward the end pieces. This can occur by initially placing self-fixating tips 16 at supportive tissue during surgical implantation. Next, each of adjusting sutures 31 can be actuated by pulling each tab 32 to shorten a distance between the central piece and each end piece; with each self-fixating tip 16 placed and fixed at supportive tissue, pulling tabs 32 will result in an increase in the length of the central piece (see FIG. 4 (relaxed central piece) relative to FIG. 5 (lengthened central piece)) and each of the tension indicators (by deformation and lengthening of each extensible segment 6). Each cursor 20 will move left or right toward centerline reference 19, when the central piece is lengthened and each extensible segment 6 is lengthened by non-permanent deformation of the curved undulations.

In use, each self-fixating tip 16 is placed at supportive tissue of a patient and a tissue support portion (approximately at the centerline) supports tissue; for example, implant 10 may be passed into a patient through a medial (e.g., vaginal or perineal) incision. A first self-fixating tip 16 can be placed at supportive tissue on a first side of the patient, such as at tissue of an obturator foramen. The tissue support portion of the central piece is placed to support tissue of a bladder, urethra, vaginal tissue, etc., depending on the treatment and patient condition. The second self-fixating tip can be placed at supportive tissue on a second (contralateral) side of the patient, such as at an opposing obturator foramen. Upon placing each self-fixating tip 16 as desired, and upon placing the tissue support portion of the central piece as desired, one or both of adjusting sutures 31 can be pulled to reduce a distance between ends of the central piece, and the end pieces, by extending the length of the central piece. This also extends each tension indicator 12 and causes each cursor 20 to move toward reference 19. A surgeon may monitor the location of cursors 20 relative to reference 19 as an indication of tension present along the length of implant 10 or the central piece thereof.

Referring to FIGS. 6 and 7, implant 10 includes features in common with the three-piece implant of FIGS. 4 and 5, with certain modifications. In specific, the central piece includes reference 19 in the form of multiple vertical bands at a location near a midline of implant 10 and the central piece. Multiple bands optionally each of a different color allow for a range of positions against which cursor 20 can be viewed. Cursor 20 is a molded or cut structure at a location of inextensible segment 8, as illustrated, a round molded or cut shaped structure (a ball). A single tension indicator 12 is present at a location at a center of the width of the implant. In use, implant 10 of FIGS. 6 (showing an unextended state) and 7 (showing an extended state) can be used in the same manner as implant 10 of FIGS. 4 and 5.

Referring to FIG. 8, illustrated is a central piece of implant 10 that includes features in common with the central piece of FIGS. 4 and 5, with certain modifications. In specific, the central piece does not include a reference 19 or implant material 30. Instead, each of the upper and lower tension indicators 12 includes a set of cursors 20a and 20b. Cursors 20a are elongate markings or structures located along a length of inextensible segments 8, such as multiple lengthwise colored markings. Cursors 20b are an arrow or other shape that is molded onto, cut, or otherwise formed with or attached to inextensible segments 8. In use, each cursor 20 (a, b) functions both as a cursor 20 (a, b) relative to its own tension indicator 12, and as a reference relative to the cursor of the other tension indicator 12. Upon lengthening of the central piece, each cursor 20a and 20b will move with inextensible segment 8 in a direction toward one end of the central piece (relative to the implant material).

Because extensible portions 6 are located on opposite ends of the central piece, cursors 20a and 20b on upper indicator 12 will move in a direction opposite of cursors 20a and 20b of lower indicator 12. The movement of cursors of the upper indicator relative to cursors of the lower indicator can indicate tension in the central piece. The opposing ends of the central piece can each be attached to an end piece (not shown), e.g., through an adjusting suture (not shown). Ends of tension indicators 12 are attached to the central piece by heat-formed vertical bands 17 of melted implant material (e.g., polypropylene) 30. In use, implant 10 of FIG. 8 can be used in the same manner as implant 10 of FIGS. 4 and 5.

FIG. 9A shows implant 10 that includes tension indicators of the type specified at FIG. 8. Implant 10 of FIG. 9A is a single-piece implant that includes (in addition to multiple cursors 20a and 20b), centerline reference 19. Cursors 20 can be, e.g., a series of different colored markings. Implant 10 of FIG. 9A also includes adjusting sutures 31 at opposing ends. Adjusting sutures 31 are threaded through pores or apertures of implant material 30 in a manner such that pulling suture 31 away from implant material 30 will reduce a length of a portion of implant material 30. Implant 10 of FIG. 9A can be used in the same manner as previous implants 10, and with a step of reducing a length of implant 10 by pulling on one or both of adjusting sutures 31.

FIG. 9B shows implant 10 of FIG. 9A, with an additional feature of grommets 34 associated with adjusting sutures 31. In use, after sutures 31 are pulled as desired to adjust a length of implant material 30, grommets 34 can be advanced toward implant material 30 to fix the desired length.

FIGS. 10A and 10B show examples of tension indicators 12 fixed to implant material 30, in the form of an implant 10 or central piece, extension portion, support portion, etc., for use in a surgical implant useful for treating male or female incontinence or another condition such as vaginal prolapse, rectal or anal prolapse, fecal incontinence, or a condition of a pelvic floor. FIG. 10B shows a set of upper and lower tension indicator 12, which can be used in any type of surgical implant by attaching ends 4 to the implant in a relaxed state.

Tension indicators as featured at the preceding figures include examples having one or multiple cursors, or combinations of one or more cursors and references, all being embodied on a middle segment of the tension indicator, e.g., at an inextensible segment. Alternately, a tension indicator can be useful having just a single location, marking, or structure designated or capable of performing a function of a cursor, e.g., relative to a reference marking (e.g., a color marking or physical structure such as a centerline, arrow, bar, or bead) located on an implant or on another tension indicator associated with the implant. Relative movement of a single cursor (e.g., a location, marking, color, or structure such as an arrow, angle, bend, kink, curve, point, extension, needle, corner, or bead) on the tension feedback indicator relative to the reference marking on the implant, or relative to another cursor associated with the implant, can indicate a tension of an implant material to which the tension indicator is attached.

An alternate or additional embodiment of an implant and tension indicator can include an implant material that contains a polymeric component such as a polymer film that changes color when a tension force is applied. Such a polymer may be used to construct an implant material, or may be attached to or otherwise incorporated into an implant or implant material to provide a change in color of the material upon application of a defined tension load. The polymer (e.g., film) can be a known polyacetylene or other material adapted to change color in response to a change in applied tension. A strip of such a polymer film or fiber can be incorporated within an implant material, or implant, e.g., in a length-wise direction, such as from end to end. When the implant material or implant is tensioned, the polymer is also placed under tension and will change color. The color change (which is generally reversible) provides instant feedback to the user as to the level of tensioning achieved. The color level can be developed and validated to provide physicians with a consistent level of tensioning and a highly effective level of tensioning upon deployment of the sling or implant.

The disclosed systems, their various components, structures, features, materials and methods may have a number of suitable configurations as shown and described in the previously-incorporated references. Various methods and tools for introducing, deploying, anchoring and manipulate device, implants, and the like as disclosed in the previously-incorporated references are envisioned for use with the present invention as well.

The various implants, systems, features, and methods detailed herein are envisioned for use with many known implant and repair systems (e.g., for male and female), features and methods, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2002/151762 and 2002/147382 and Applicant's co-pending PCT patent application PCT/US2012/026888, filed Feb. 28, 2012. The above-identified disclosures are fully incorporated herein by reference in their entirety.

All patents, patent applications, and publications cited herein are hereby incorporated by reference in their entirety as if individually incorporated, and include those references incorporated within the identified patents, patent applications and publications.

The invention claimed is:

1. An implant material comprising:
    a first tension indicator,
    the implant material having a first implant material end, a second implant material end, a length of implant material between the first implant material end and the second implant material end, wherein the length of implant material can be increased and decreased,
    the first tension indicator extending along a continuous portion of the length of implant material, the first tension indicator including:
        a first end fixed relative to a first position of the continuous portion,
        a second end fixed relative to a second position of the continuous portion,
        a first middle segment extending along the continuous portion between the first position and the second position, the middle segment comprising an extensible segment and an inextensible segment, and
        a first cursor located at the middle segment,
    wherein when the length of implant material between the first position and the second position is increased, the first cursor moves in a first direction relative to a reference, and when the length of the implant material is decreased, the first cursor moves relative to the reference in a direction opposite the first direction; and
    wherein the implant material comprises a second tension indicator including:
        a first end fixed relative to a third position of the continuous portion, a second end fixed relative to a fourth position of the continuous portion,
a second middle segment extending along a length between the third position and the fourth position, and
a second cursor located at the second middle segment, wherein when the length of implant material between the third position and the fourth position is increased, the second cursor moves in a first direction relative to the reference, and when the length of the implant material is decreased, the second cursor moves relative to the reference in a direction opposite the first direction.

2. The implant material according to claim 1, wherein when the implant material is lengthened, the first cursor moves in a longitudinal direction relative to the reference.

3. The implant material according to claim 1, wherein the reference comprises a marking on the implant material.

4. The implant material according to claim 3, wherein the marking comprises a colored marking at a centerline.

5. The implant material according to claim 3, wherein the reference comprises multiple colored markings.

6. The implant material as recited at claim 1, wherein the extensible segment is selected from the group consisting of: a linear elastomeric material, and a deformable structure that includes a deformable non-linear segment.

7. The implant material as recited at claim 1, wherein the inextensible segment is an elongate segment selected from: a polymeric line, a metal wire, and a fiber line.

8. The implant material as recited at claim 1, wherein the first cursor is located on the inextensible segment.

9. The implant material according to claim 1, wherein the first cursor comprises a colored marking located on the inextensible segment.

10. The implant material according to claim 1, wherein the reference includes a marking on the implant material.

11. A surgical implant comprising the implant material of claim 1, wherein the surgical implant is a urethral sling comprising:
an extensible mesh implant material comprising a tissue support portion and two extension portions extending away from the tissue support portion, and
two self-fixating tips, one at an end of each extension portion, wherein the urethral sling has a length between the two ends and a midpoint along the length, and the first tension indicator is located against a surface of the surgical implant that includes the midpoint.

12. A surgical implant comprising the implant material of claim 1, wherein the surgical implant is an adjustable three-piece implant comprising a central piece and two extension pieces,
the central piece comprising a tissue support portion and the first tension indicator, and each extension piece comprising a proximal end and a distal end, each proximal end being adjustably engaged with the central piece and each distal end comprising a tissue fastener.

13. A method of treating urinary incontinence, comprising:
providing a surgical implant comprising the implant material according to claim 1,
creating a medial incision in a male or female patient,
dissecting from the medial incision to tissue below a urethra,
placing the surgical implant at a location to support the urethra,
placing a first end of the surgical implant along a tissue path extending from below the urethra toward a first obturator foramen of the patient,
placing a second end of the surgical implant along a tissue path extending from below the urethra toward a second obturator foramen of the patient, and
viewing the first tension indicator.

14. The implant material according to claim 1, wherein the reference is located on the continuous length of implant material.

15. The implant material according to claim 1, wherein the implant material is mesh.

16. An implant material comprising:
extensible implant material having a first implant material end, a second implant material end, a length between the first implant material end and the second implant material end, wherein the length of implant material can be increased and decreased,
a first tension indicator located along a continuous portion of the length of the implant material, wherein the first tension indicator includes:
a first end connected to the implant material,
a second end connected to the implant material,
a middle segment extending along the continuous portion between the first end of the first tension indicator and the second end of the first tension indicator, the middle segment comprising an inextensible segment, an extensible segment, and a first cursor on the inextensible segment,
a second tension indicator located along the continuous portion, and
a reference.

17. The implant material according to claim 16, wherein the second tension indicator comprises:
a first end connected to the extensible implant material,
a second end connected to the extensible implant material,
a middle segment comprising an inextensible segment, an extensible segment, and a second cursor on the inextensible segment, and
the reference is a marking on the extensible implant material.

18. The implant material according to claim 17, wherein when the implant material is lengthened, the first tension indicator is lengthened, the second tension indicator is lengthened, and the first cursor of the first tension indicator moves relative to the second cursor of the second tension indicator.

19. The implant material according to claim 16, wherein the extensible segment is lengthened as the first tension indicator is lengthened from an original state, and the extensible segment returns to an un-lengthened state as the first tension indicator returns to the original state.

20. A method of assembling a surgical implant, the method comprising:
providing an extensible implant material, having a first implant material end, a second implant material end, a continuous length between the first implant material end and the second implant material end, wherein the continuous length of implant material can be increased and decreased,
providing a first tension indicator including:
a first end, a second end, and a middle segment between the first end and the second end, the middle segment comprising an extensible segment and an inextensible segment,
placing the first tension indicator along a portion of the continuous length of the extensible implant material,
fixing the first end relative to a first position of the extensible implant material, and fixing the second end relative to a second position of the extensible implant material;
providing a second tension indicator including:
  a first end, a second end, and a middle segment between the first end and the second end, the middle segment comprising an extensible segment and an inextensible segment,
placing the second tension indicator along a portion of the continuous length of the extensible implant material,
fixing the first end of the second tension indicator relative to a third position of the extensible implant material, and
fixing the second end of the second tension indicator relative to a fourth position of the extensible implant material.

* * * * *